United States Patent
Atta et al.

(10) Patent No.: US 12,311,013 B1
(45) Date of Patent: May 27, 2025

(54) GELS FOR INSULIN DELIVERY

(71) Applicant: KING SAUD UNIVERSITY, Riyadh (SA)

(72) Inventors: Ayman M. Atta, Riyadh (SA); Wasmiah Mohammed Abdu Dahan, Riyadh (SA); Hissah Hamad Al-Tilasi, Riyadh (SA); Hamad A. Al-Lohedan, Riyadh (SA); Abdelrahman O. Ezzat, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/025,220

(22) Filed: Jan. 16, 2025

(51) Int. Cl.
| | |
|---|---|
| *A61K 38/28* | (2006.01) |
| *A61K 9/06* | (2006.01) |
| *A61K 47/32* | (2006.01) |
| *A61K 47/36* | (2006.01) |
| *A61K 47/46* | (2006.01) |

(52) U.S. Cl.
CPC ............... *A61K 38/28* (2013.01); *A61K 9/06* (2013.01); *A61K 47/32* (2013.01); *A61K 47/36* (2013.01); *A61K 47/46* (2013.01)

(58) Field of Classification Search
None
See application file for complete search history.

(56) References Cited

U.S. PATENT DOCUMENTS 5,603,955 A * 2/1997 Gehrke ............... A61K 9/2095
516/107

FOREIGN PATENT DOCUMENTS

| IN | 202141056711 A | 12/2021 |
|---|---|---|
| JP | 09012463 * | 1/1997 |

OTHER PUBLICATIONS

Lopez et al. (Effect of formulation variables on oral grittiness and preferences of multiparticulate formulations in adult volunteers, European Journal of Pharmaceutical Sciences, 92 (2016) 156-162). (Year: 2016).*
Medline Plus (Diabetes-insulin therapy, May 12, 2023). (Year: 2023).*
Arora, et al.; "EMULGEL: A Novel Approach for Hydrophobic Drugs"; International Journal of Pharmacy and Biological Sciences ISSN: 2321-3272 (Print), ISSN: 2230-7605 (Online) IJPBS | vol. 7 | Issue 3 | Jul.-Sep. 2017 | 43-60.
Soliman, et al.; Enhancement of Curcumin Anti-Inflammatory Effect via Formulation into Myrrh Oil-Based Nanoemulgel, Enhancement of Curcumin Anti-Inflammatory Effect via Formulation into Myrrh Oil-Based Nanoemulgel. Polymers 2021, 13, 577. https://doi.org/10.3390/polym13040577 Published: Feb. 14, 2021.
Avadi, et al.; "Ex Vivo Evaluation of Insulin Nanoparticles Using Chitosan and Arabic Gum", International Scholarly Research Network ISRN Pharmaceutics vol. 2011, Article ID 860109, 6 pages doi:10.5402/2011/860109 Received Apr. 4, 2011; Accepted May 5, 2011.
Froelich, et al.; "Natural Gums in Drug-Loaded Micro- and Nanogels", Chair and Department of Pharmaceutical Technology, Poznan University of Medical Sciences, Grunwaldzka 6, 60-780 Poznan, Poland T. Natural Gums in Drug-Loaded Micro- and Nanogels. Pharmaceutics 2023, 15, 759. https://doi.org/10.3390/pharmaceutics15030759.
Sagbas, et al.; "Modifiable natural gum based microgel capsules as sustainable drug delivery systems", Faculty of Science & Arts, Chemistry Department & 2Nanoscience and Technology Research and Application Center (NANORAC), Canakkale Onsekiz Mart University, Terzioglu Campus, 17100 Canakkale, Turkey. Accepted date: Jul. 27, 2018.

* cited by examiner

*Primary Examiner* — Melissa S Mercier
(74) *Attorney, Agent, or Firm* — Nath, Goldberg & Meyer; Joshua B. Goldberg

(57) ABSTRACT

A synthesized gel including an extract selected from the group consisting of Gum Arabic (GA) extract, myrhh (MR) extract, a polymer or monomer selected from the group consisting of NIPAm and acidic monomers; APS initiator; MBA; and insulin. A method of treating insulin dependent diabetes includes administering to a patient in need thereof a therapeutically effective amount of the insulin loaded into the gel.

14 Claims, 19 Drawing Sheets

GELS FOR INSULIN DELIVERY

BACKGROUND

1. Field

The present disclosure relates to gels for insulin delivery, and more particularly, to gels including gum Arabic (GA) and myrrh (MR) for oral delivery of insulin.

2. Description of the Related Art

Insulin is the most effective drug, currently available, to treat individuals with insulin dependent Type 1 diabetes. Insulin injections are generally disliked by patients for a number of reasons, such as, fear of needles, pain caused by injections, skin bulges caused by insulin injections, allergic reactions to the insulin injections, risk of infections from the injections, and stress caused by the difficult long-term regimen of insulin injection therapy. To address these concerns, researchers have focused on ways to deliver insulin to patients without injections, rather than developing insulin alternatives.

Previously, a chewable gum with an insulin formulation based on mixing of the liposomal insulin in the presence of guar gum, beeswax, powdered acacia, oleic acid, gamma-linoleic acid and sorbitol was used. Alternatively, natural polymers such as guar gum and acacia gum provide a hydrogel-forming polymer for use as a protein carrier and administered through oral and nasal membranes. Natural polymers are nontoxic, biodegradable, inexpensive and can be formulated and modified to act as protein carriers for oral administration.

Thus, a method of delivering insulin to a patient which solves the afore-mentioned problems is desired.

SUMMARY

The present disclosure relates to gels including an extract selected from the group consisting of Gum Arabic (GA) extract and Myrrh (MR) extract. The extract is modified with polymerizable protic ionic liquids by grafting and crosslinking using a surfactant free method. In an embodiment, the gels can be amphiphilic nanogels which can be loaded with insulin for oral administration. The insulin-loaded gels can protect the insulin from degradation by stomach fluids and from release in the intestines and the duodenum. As described herein, insulin release data of modified GA nanogels demonstrate that the nanogels are ideal for oral insulin delivery to treat insulin dependent Type I diabetes.

In an embodiment, the present disclosure relates to a synthesized gel including an extract selected from the group consisting of Gum Arabic (GA) extract and myrrh (MR) extract; a polymer or monomer selected from the group consisting of N-Isopropylacrylamide (NIPAm) and acidic monomers; ammonium persulfate (APS) initiator; N,N'-methylenebisacrylamide (MBA); and insulin.

In some embodiments, the synthesized gels include a polyvinyl selected from the group consisting of quaternized VIm and 4-VP organic salts.

In an embodiment, the present subject matter relates to a method of treating insulin dependent diabetes, including administering to a patient in need thereof a therapeutically effective amount of insulin loaded in the gels described herein.

These and other features of the present subject matter will become readily apparent upon further review of the following specification.

DETAILED DESCRIPTION OF THE PREFERRED EMBODIMENTS

Figure 1A:
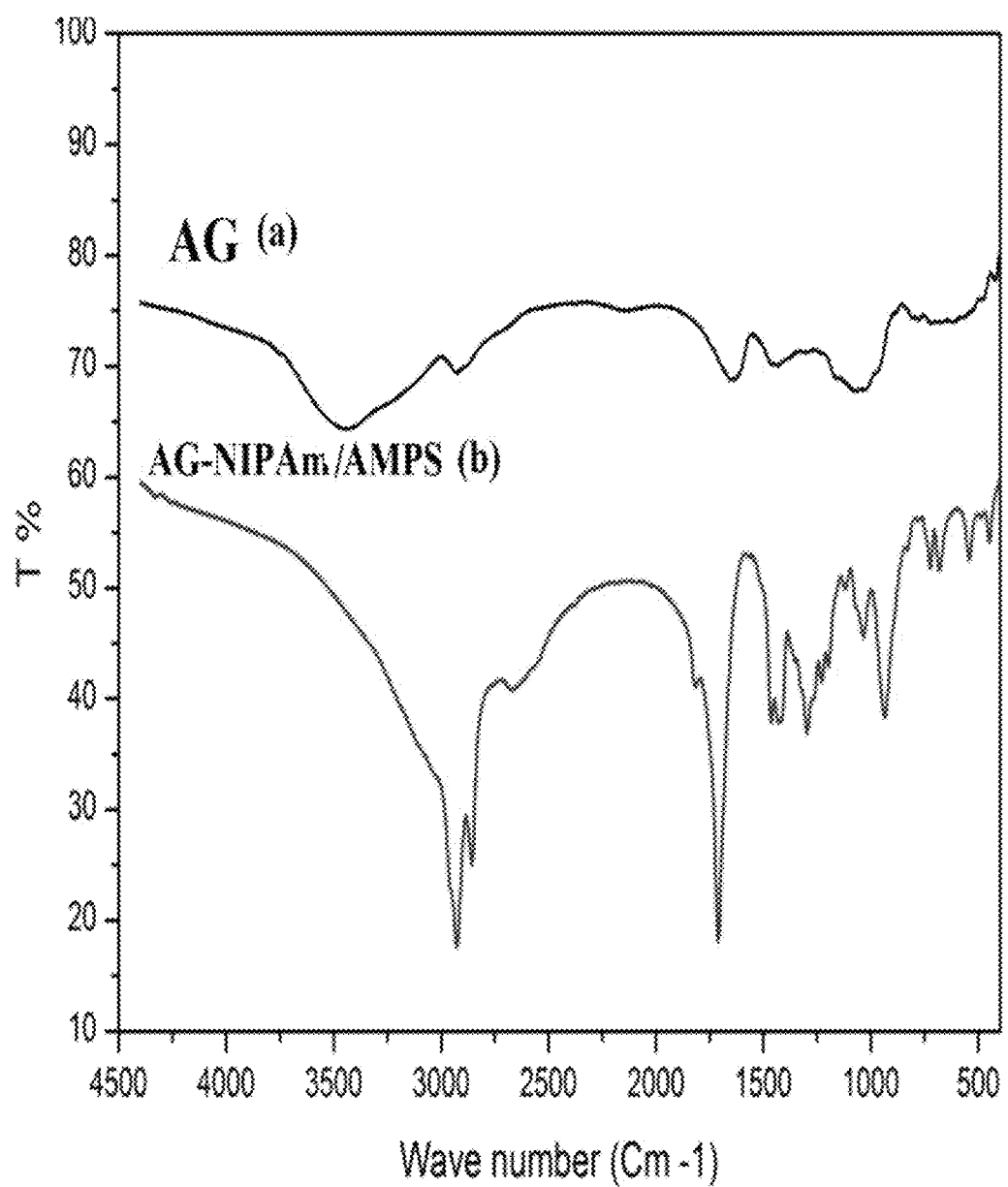
FIG. 1A is a FTIR spectra of GA nanogels, particularly (a) GA and (b) GA-NIPAm/AMPS.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as insulin dependent Type 1 diabetes.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to gels including gum Arabic (GA) and/or myrrh. The gels can include an ionic liquid for oral delivery of insulin. The chemical structure of natural polymers in the gels are modified by the ionic liquid to protect insulin from digestion in the stomach due to the action of digestive proteases. The chemical structures of the natural polymers are modified to be biocompatible, pH sensitive polymers to protect insulin at the pH of the stomach and to release it at intestinal pH. The insulin release is site-specific and close to the absorption surfaces to protect the insulin from intestinal proteases. Insulin release also controls blood glucose and achieves the correct physiological concentration in the blood.

In an embodiment, the sizes and morphologies of the GA grafts can be controlled using polymerizable ionic liquid monomers (P-ILs). In an embodiment, the P-ILs can be formed by reacting vinyl imidazole or vinyl pyridine monomers with acidic monomers, such as acrylic acid, methacrylic acid, or 2-acrylamido-2-methylpropane sulfonic acid monomers. In an embodiment, the P-ILs can be grafted onto the surface of the GA in the presence of alkyl acrylamide monomers having lower critical solution transition temperature (LCST), below grafting temperature, such as N-isopropylacrylamide (NIPAm). The resulting gel can be used as an insulin oral delivery system at body temperature (37° C.).

According to an embodiment, the gel, loaded with insulin, can include an extract selected from the group consisting of Gum Arabic (GA) and myrhh (MR); a polymer; and a monomer selected from the group consisting of N-Isopropylacrylamide (NIPAm) and acidic monomers; ammonium persulfate (APS) initiator; N,N'-methylenebisacrylamide (MBA); and insulin.

In an embodiment, the gel may include a polyvinyl selected from the group consisting of quaternized N-vinyl imidazole (VIm) or 4-vinyl pyridine (4-VP) organic salt.

In certain embodiments, the acidic monomers may be selected from the group consisting of 2-acrylamido-2-methyl-1-propanesulfonicacid (AMPS), acrylic acid (AA), and methacrylic acid (MAA).

In further embodiments, the gels may include a microgel. In other embodiments, the gels may include a nanogel.

In certain embodiments, the gel includes gum Arabic (GA) extract. In one embodiment, the gel includes gum Arabic (GA) extract, N-Isopropylacrylamide (NIPAm) and 2-acrylamido-2-methyl-1-propanesulfonicacid (AMPS) (GA-NIPAm/AMPS). In an embodiment, gel particles may have a diameter of about 1950 nm. In some embodiments, the gels may have an insulin encapsulation efficiency of about 100% at about 24 hours.

In other embodiments, the gel includes gum Arabic (GA) extract, N-Isopropylacrylamide (NIPAm), N-vinyl imidazole (Vim), and 2-acrylamido-2-methyl-1-propanesulfonicacid (AMPS) (AG-NIPAm/VIm-AMPS). In an embodiment, gel particles may have a diameter of about 191 nm. In embodiments, an insulin encapsulation efficiency of the gel may be 75% at 5 hours.

In still other embodiments, the gel includes Arabic (GA) extract, N-Isopropylacrylamide (NIPAm), 4-vinyl pyridine (4-VP), and 2-acrylamido-2-methyl-1-propanesulfonicacid (AMPS) (AG-NIPAm/4-VP-AMPS). In an embodiment, the gel particles may have a diameter of about 321 nm. In certain embodiments, an insulin encapsulation efficiency of the gel may be 70% at 10 hours.

In certain embodiments, the gel includes MR extract, N-Isopropylacrylamide (NIPAm), and 2-acrylamido-2-methyl-1-propanesulfonicacid (AMPS) (MR-NIPAm/AMPS). In an embodiment, the gel particles may have a diameter of about 1212 nm. In certain embodiments, an insulin encapsulation efficiency of the gel may be 52% at 24 hours.

In still another embodiment, the present subject matter may relate to a method of treating insulin dependent diabetes, the method may include administering to a patient in need thereof a therapeutically effective amount of insulin loaded in the gel described herein.

In further embodiments, the method may include administering the gel orally.

In a first embodiment, the present gels may be prepared according to the following method. Specifically, synthesis can commence with dissolving gum Arabic (AG) or myrrh (MR) extracts in distilled water. The extracts may be dissolved in the presence of either N-Isopropylacrylamide (NIPAm) or acidic monomers (2-acrylamido-2-methyl-1-propanesulfonicacid (AMPS), acrylic acid (AA), or methacrylic acid (MAA)), under nitrogen atmosphere. Ammonium persulfate (APS) as a grafting radical initiator and N,N'-methylenebisacrylamide (MBA) may be added and dissolved at a temperature of at least about 40° C. for at least about 1 hour. The reaction temperature may be increased and heated to a temperature of at least about 60° C. to at least about 100° C. for at least about 1 hour to at least about 6 hours. Half the reaction solution may be evaporated and then ethanol may be added to obtain a turbid solution. The turbid solution may precipitate by either centrifuging at 8000 rpm for at least about 30 minutes or through a freeze-drying technique.

In a second embodiment, the present gels may be prepared according to another method. Specifically, different mole ratios of acidic monomers, based on AMPS, AA, or MAA, may be blended with NIPAm. A first half of an amount of NIPAm may be solubilized with purified AG or MR powder in distilled water at a reaction temperature of at least about 40° C. to obtain a turbid solution. A second half of the amount of NIPAm, AA or NIPAm, MAA may be mixed with APS initiator and MBA in distilled water to provide a mixture. The mixture may be heated to a temperature range of at least about 40° C. to at least about 100° C. under nitrogen gas for at least about 1 hour. The temperature of the reaction may be maintained for at least about 4 hours. Then, the reaction temperature may be increased to a range of about 60° C. to at least about 100° C. for at least about 1 hour to at least about 6 hours. Half of the reaction solution may then be evaporated, and ethanol may be added to obtain a turbid solution which can be precipitated either by centrifuging at 8000 rpm for at least about 30 minutes or by using a freeze-drying technique.

In an embodiment, the gels may be prepared by stirring a mixture of AMPS, MAA, or AA with VIm or 4-VP under nitrogen atmosphere at a temperature of at least about 10° C. in a flask. The mixing may be carried out for at least about 5 hours to complete dissolution of AMPS in N-vinyl imidazole (Vim) or 4-vinyl pyridine (4-VP) solutions to obtain a transparent solution. The transparent solution may form due to the formation of quaternized VIm or 4-VP organic salts with AA and AMPS monomers. Different mole ratios of quaternized VIm or 4-VP organic salt may then be blended with NIPAm. A first half of an amount of NIPAm may be solubilized with purified AG or MR powder in distilled water at a reaction temperature of at least about 40° C. to obtain a turbid solution. A second half of the amount of NIPAm, quaternized VIm or 4-VP organic salt may be mixed with APS initiator and MBA in distilled water. The mixture may be heated to at least about 40° C. to about 100° C. under nitrogen gas for at least about 1 hour. The reaction may be kept at temperature for at least about 4 hours. Then the reaction temperature may be increased to about 60° C. to at least about 100° C. for at least about 1 hour to at least about 6 hours. Half of the reaction solution may then be evaporated. Ethanol may then be added to obtain a turbid solution. The turbid solution may be precipitated either by centrifuging at 8000 rpm for 30 minutes or using a freeze-drying technique. The described method is outlined in Schemes 1 and 2 below.

Scheme 1: Functionalization of AG with NIPAm/VIM-AMPS

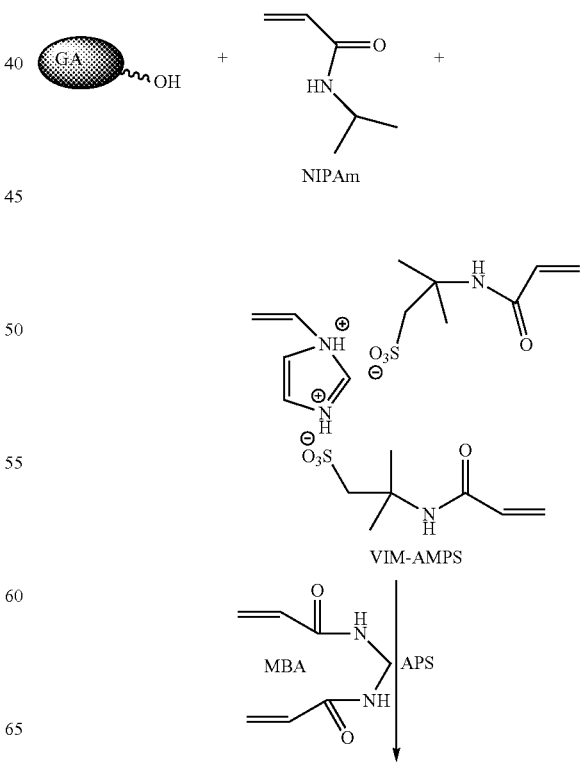

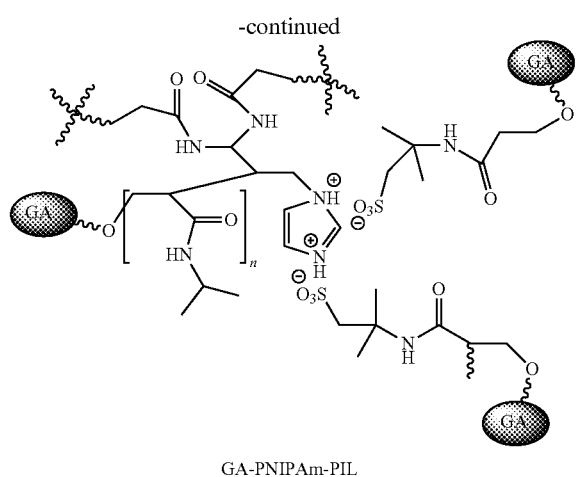

GA-PNIPAm-PIL

Scheme 2: Functionalization of AG with NIPAm/4-VP-AMPS

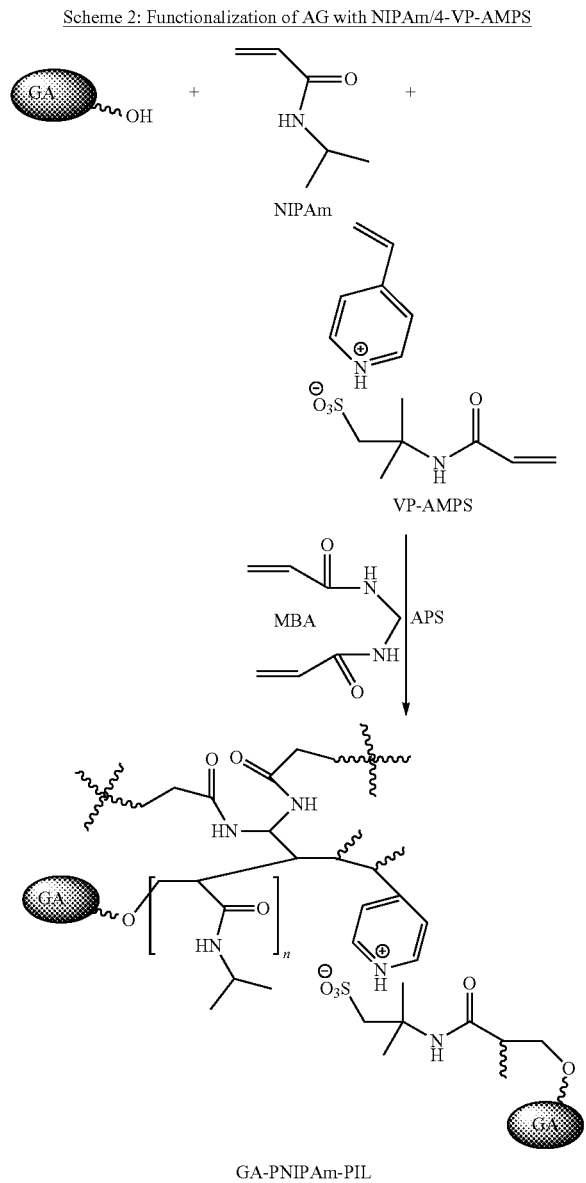

GA-PNIPAm-PIL

Insulin loading of the gels may be accomplished by immersing the synthesized modified gels prepared by the methods above in an insulin solution under stirring for at least about 24 hours at room temperature. The gel suspension may be filtered and washed with deionized water.

The present gels may be administered at a therapeutically or pharmaceutically effective dosage of insulin, e.g., a dosage sufficient to provide treatment for Type 1 diabetes.

EXAMPLES

Materials

N-Isopropylacrylamide (NIPAm; 99%, Sigma Aldrich), 2-acrylamido-2-methyl-1-propanesulfonicacid (AMPS; 99%, Sigma Aldrich), acrylic acid (AA; 99%, Sigma Aldrich), methacrylic acid (MAA; 99%, Sigma Aldrich), N-vinyl imidazole (VIm; 99%, Sigma Aldrich), N,N'-methylenebisacrylamide (MBA; Sigma Aldrich) and 4-vinyl pyridine (4-VP 99%, Sigma Aldrich) were used as purchased without purification. Ammonium persulfate (APS) was used for a grafting radical initiator.

Insulin aspart NovoRapid® Flex Pen where each 1 mL contains 100 unit of insulin was used as the insulin source. Dialysis membrane (MWCO 14000, Spectra/pro) was used to estimate the insulin release at different pHs. Buffer solutions were used to study the insulin release.

The synthetic stomach fluid (SSF) was prepared using HCl (0.42 M), glycine (0.40 M) in deionized water to adjust pH to 1.2. The simulated intestinal fluid (SIF) was prepared by dissolving one buffer tablet of pH 9 in 200 mL of deionized water and the pH of the solution was adjusted at 7.4 using HCl (1M).

Example 1

Preparation of Gum Arabic and Myrrh

Gum Arabic (GA) and Myrrh (MR) were procured from a commercial market in Riyadh, Saudi Arabia. Myrrh resin was ground in a mortar and extracted using water:ethanol (1:1 volume %) using Soxhlet extraction for 24 hours. The extract was filtered to separate the undissolved solids, and the water/ethanol solvents were removed under reduced pressure to produce water ethanol soluble powder. GA powder (100 g) was dissolved in 200 mL of distilled water under stirring for 24 hours and then filtered to remove impurities. The gum supernatant was precipitated by adding 350 mL of 96% ethanol, filtered, collected and air dried.

Example 2

Homopolymer GA and MR Grafts Microparticles (Method 1)

GA or MR extracts (2 g) were dissolved in distilled water (200 mL) in the presence of either NIPAm or acidic monomers (2 g; AMPS, AA, or MAA) under nitrogen atmosphere. The APS initiator (0.01-1 g), MBA (0.01-1 g) was added and dissolved at a temperature of 40° C. for 1 hour. The reaction temperature was increased and heated at 60-100° C. for 1-6 hours. Half of the reaction solution was evaporated, and ethanol was added to obtain a turbid solution which precipitated either with centrifuging at 8000 rpm for 30 minutes or freeze-drying technique.

Example 3

Acidic Copolymer GA and MR Grafts Micro and Nanoparticles (Method 2)

Different mole ratios of acidic monomers based on AMPS, AA, or MAA (2 g; 5-50 mol %) were blended with NIPAm (2 g; 50-95 mol %). A first half of the amount of NIPAm was solubilized with purified GA or MR powder (2 g) in distilled water (200 mL) at the reaction temperature of 40° C. to obtain a turbid solution. The second half of the amount of NIPAm, AA or NIPAm, MAA was mixed with APS initiator (0.01-1 g), and MBA (0.01-1 g) in 50 mL of distilled water and added to the reaction temperature after heating the reaction temperature from 40 to 100° C. under nitrogen gas for 1 hour. The reaction temperature was kept constant for 4 hours. Then, the reaction temperature was increased and heated at 60-100° C. for 1 to 6 hours. Half of the reaction solution was evaporated, and ethanol was added to obtain a turbid solution which precipitated either with centrifuging at 8000 rpm for 30 minutes or freeze-drying technique.

Example 4

Ionic Liquid GA and MR Grafts Micro and Nanoparticles (Method 3)

A mixture of equal molar ratios (1:1 mol %) of AMPS, MAA or AA (6 mmol of each monomer) was stirred with 12 mmol of VIm or 4-VP under nitrogen atmosphere at 10° C. in a flask. The mixing was carried out for 5 hours to complete dissolution of AMPS in VIm or 4-VP solutions to obtain a transparent solution due to the formation of quaternized VIm or 4-VP organic salt with AA and AMPS monomers. Different mole ratios of quaternized VIm or 4-VP organic salt (2 g; 5-50 mol %) were blended with NIPAm (2 g; 50-95 mol %). The first half amount of NIPAm was solubilized with purified GA or MR powder (2 g) in distilled water (200 mL) at the reaction temperature of 40° C. to obtain a turbid solution. The second half amount of NIPAm, quaternized VIm or 4-VP organic salt was mixed with the APS initiator (0.01-1 g), and MBA (0.01-1 g) in 50 mL of distilled water and added to the reaction temperature after heating the reaction temperature from 40 to 100° C. under nitrogen gas for 1 hour. The reaction temperature was kept constant for 4 hours. The reaction temperature was increased and heated at 60-100° C. for 1-6 hours. Half of the reaction solution was evaporated, and ethanol was added to obtain a turbid solution which precipitated either with centrifuging at 8000 rpm for 30 minutes or a freeze-drying technique.

Example 5

Characterization of GA and MR Gels

The chemical structures of different types of GA or MR microgels and nanogels were elucidated by Fourier Transform Infrared Spectroscopy (FT-IR; a Shimadzu IRTracer-100 FT-IR spectrometer). Thermal stability of GA or MR microgels and nanogels was determined from thermogravimetric and differential thermogravimetric analysis (TGA-DTG; TGA-50 SHIMADZU) using $N_2$ at a heating rate of 10° $C.min^{-1}$, respectively. The particle size and polydispersity index (PDI) of modified different types of GA or MR microgels and nanogels dispersions in water and 0.001 M KCl were investigated using dynamic light scattering (DLS; Malvern Instrument Ltd., London, UK). The surface charges of GA or MR microgels and nanogels dispersions in water were determined by using Zetasizer Nano ZS, Malvern Instrument Ltd., Malvern, UK. The morphologies of modified types of GA or MR microgels and nanogel dispersions were evaluated from the transmission electron microscopy (TEM; JEOL JEM-2100F with an acceleration voltage of 200 kV, Tokyo, Japan). The surface morphologies were investigated using (SEM; JEOL JXA-840A instrument at 5-20 kV). Ultraviolet spectrophotometer (UV2100, Shimadzu) was used to determine the concentrations of free insulin using Lowry's method at 284 nm.

Figure 1B:
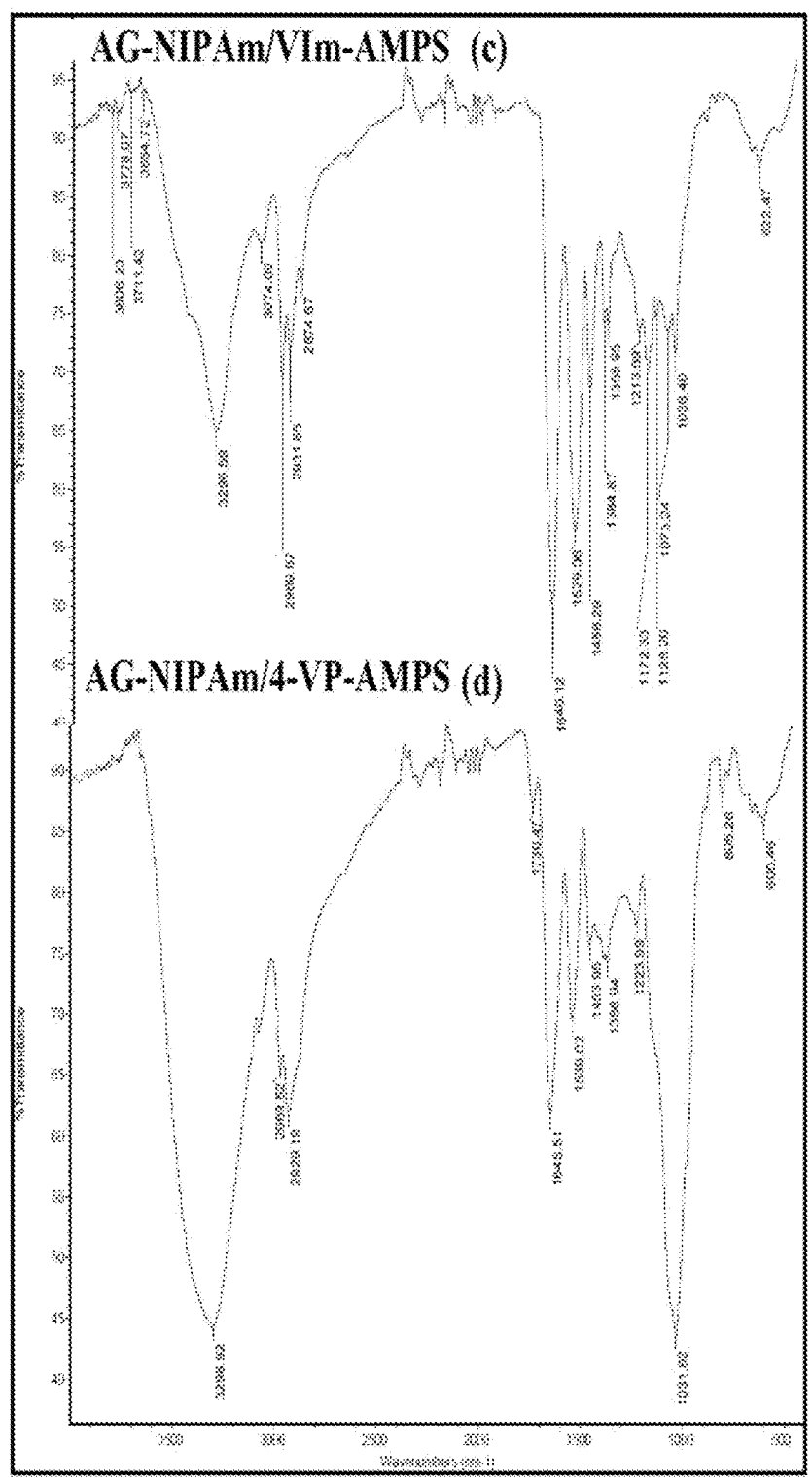
FIG. 1B is a FTIR spectra of GA nanogels, particularly (c) GA-NIPAm/VIm-AMPS and (d) GA-NIPAm/4-VP-AMPS.
Figure 2:
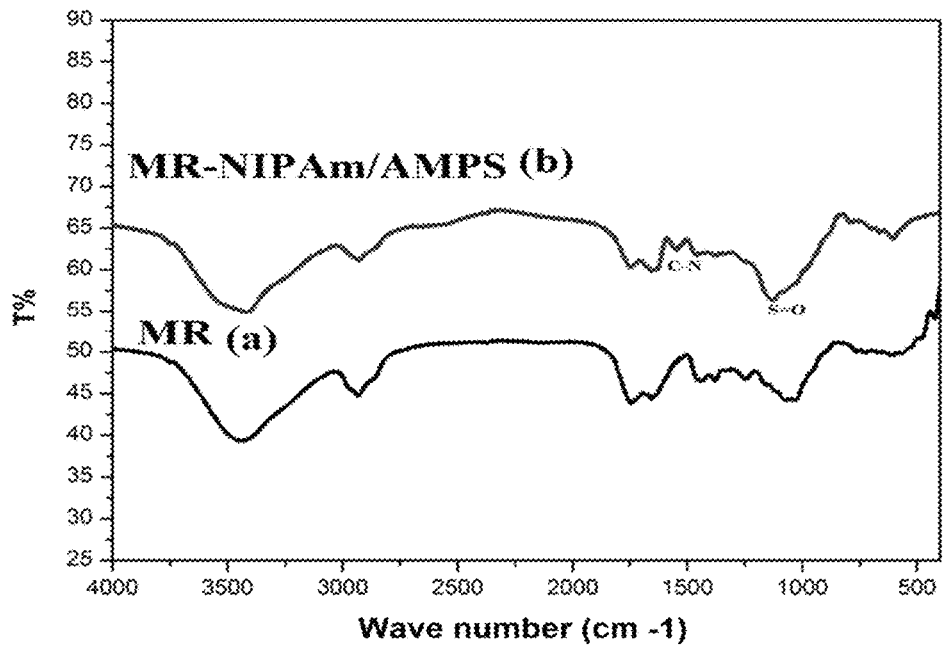
FIG. 2 is a FTIR spectra of MR nanogels, particularly (a) MR and (b) MR-NIPAm/AMPS.

The chemical structures of the modified GA and MR nanocomposites prepared by methods 2 and 3 were selected and represented in FIGS. 1 and 2. The characteristic bands of polysaccharides were confirmed from FTIR spectrum of GA (a) in FIG. 1A from the appearance of broad bands at 3650, 2950, 1720, 1618, 1150 cm-1 that attributed to OH, CH aliphatic, C═O aldehyde, N—H and C—N or C—O stretching vibration, respectively. The crosslinking of GA with (NIPAm/AMPS; 90/10 mol %) was confirmed from its spectrum (b) in FIG. 1A from the appearance of bands at 1690, 1632, 1428, 1297, 1201 and 1170 cm-1 corresponding to the amide C═O group, NH amide, —$CH_2$ bending, $CH_3$ bending, C—O and S═O stretching vibrations of NIPAm and AMPS groups. The disappearance of ═CH stretching vinyl groups of MBA, NIPAm and AMPS confirms crosslinking polymerization. Accordingly, the grafting and crosslinking of NIPAm/AMPS onto GA were confirmed as (b) in FIG. 1A of GA-NIPAm/AMPS. The grafting of NIPAm/VIm-AMPS (90/5-5 mol %) (c) and NIPAm/4-VP-AMPS (90/5-5 mol %) (d) can be elucidated from their FTIR spectra in FIG. 1B. The single bond S—O frequencies are found within the range 800-950 $cm^{-1}$, the double bond S═O stretches appear from 950 to 1300 $cm^{-1}$ whereas the S—OH bonds fall in the range 1300-1450 $cm^{-1}$. The bands at about 1150 $cm^{-1}$ exhibit various vibrations of $SO_3$ where the most intense vibration peak appears at 1143 $cm^{-1}$. As seen in the spectra of the AG-NIPAm/VIm-AMPS (FIG. 1B (c)) and GA-NIPAm/4-VP-AMPS (FIG. 1B (d)), there are bands in the range 1370-1430 $cm^{-1}$. These bands are in fact due to hydrogen bond (O—H) formation between hydrogen atoms of OH groups and oxygen atoms of $SO_3^-$ anion resulting in cluster formation as shown in Schemes 1 and 2 above.

Referring to FIG. 2, FTIR spectra of MR (a) and MR-NIPAm/AMPS (b) before and after the crosslinking are shown. Both spectra are very similar and showed bands around 1045, 1445, 1438, 1635, 2855, 2925, and 3449 $cm^{-1}$. The band around 1025 to 1200 $cm^{-1}$ corresponds to the C—O stretching, while the weak bands in the 1340 to 1450 $cm^{-1}$ range can be attributed to aliphatic $CH_2$ and $CH_3$ groups, $CH_2$ groups of aldehydes and ketones, and the bending modes of O—H bonds in alcohols, phenols, and carboxylic acids. The new bands appeared at around 1620 and 1150 $cm^{-1}$ assigned to C—N and S═O stretching vibrations of NIPAm-AMPS (b).

Figure 3A:
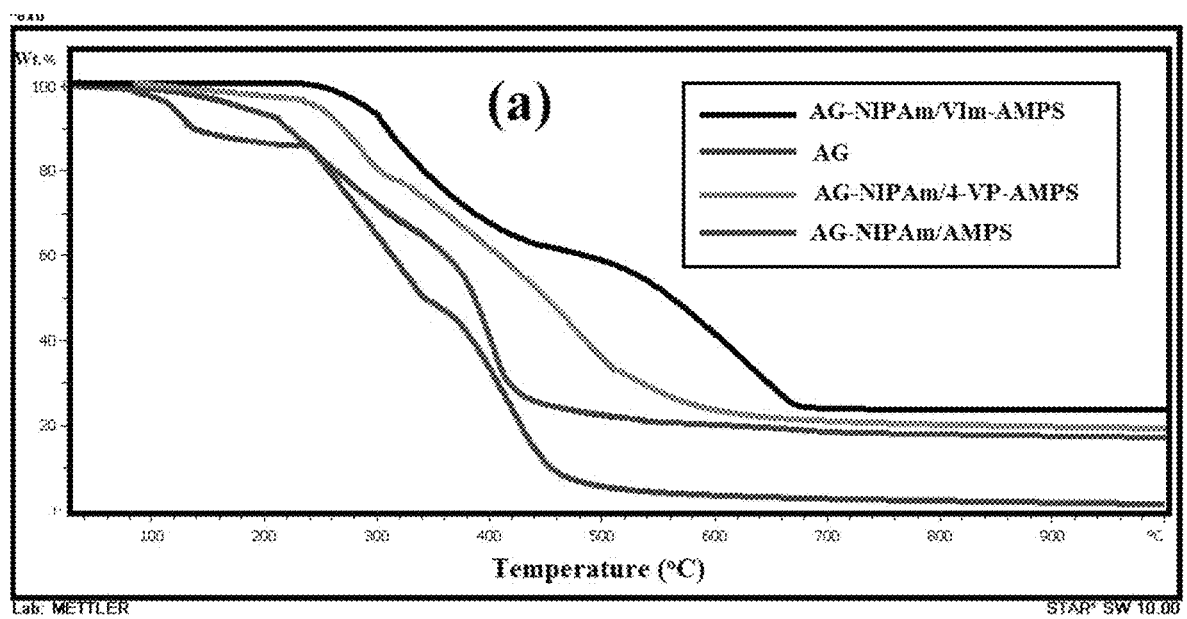
FIG. 3A is a thermogravimetric analysis (TGA) graph of GA nanogels.
Figure 3B:
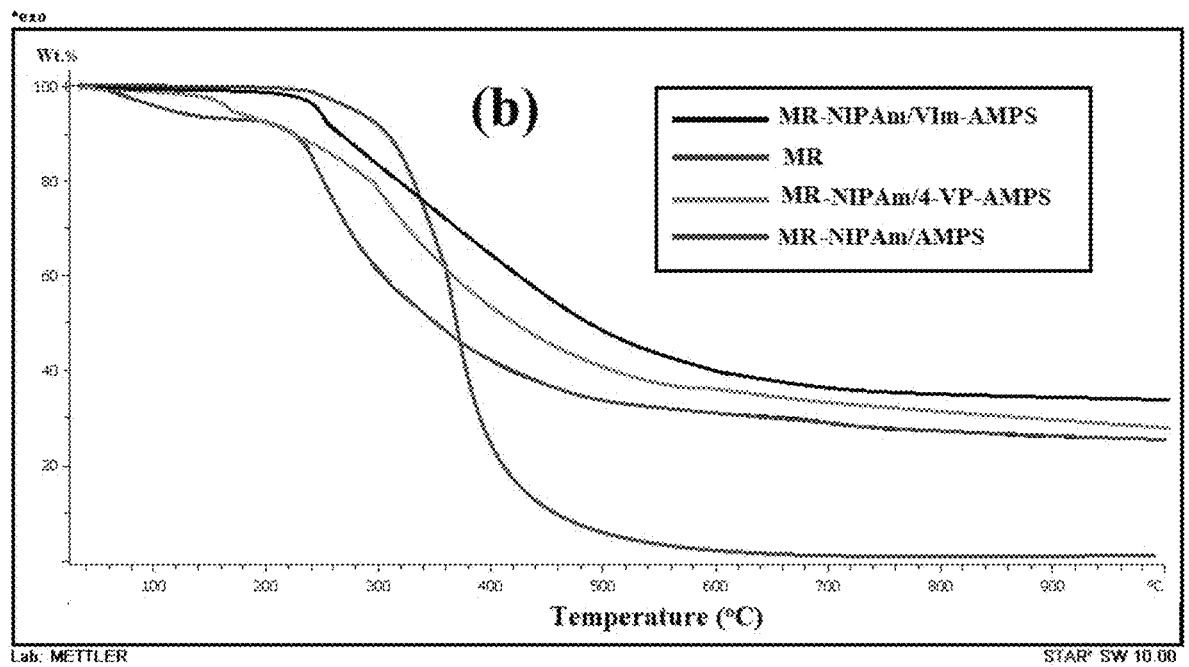
FIG. 3B is TGA graph of MR nanogels.
Figure 4A:
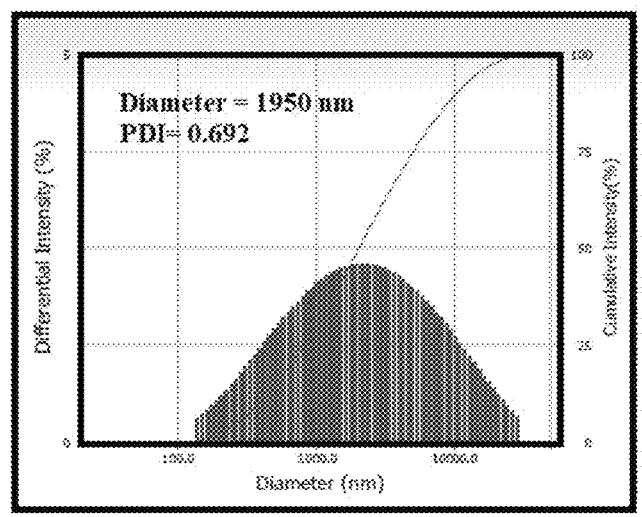
FIG. 4A is a data light scattering (DLS) graph showing particle size of GA-NIPAm/AMPS gels.
Figure 4B:
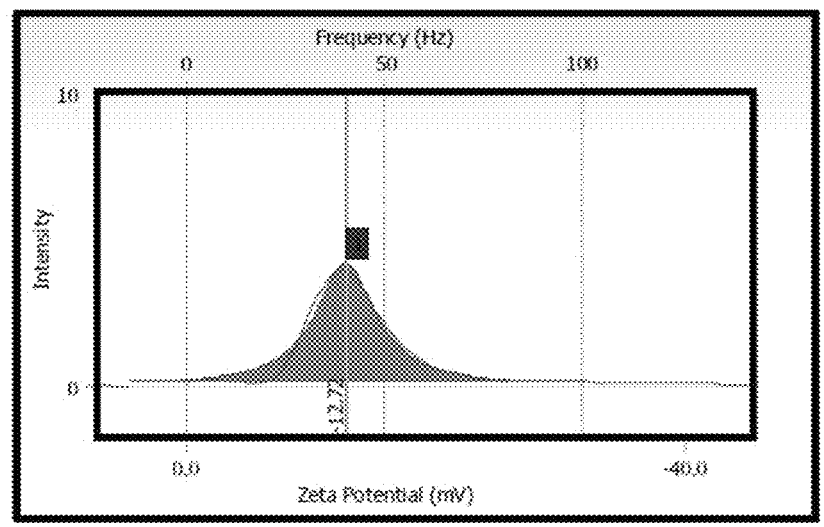
FIG. 4B is a DLS graph showing zeta potential of GA-NIPAm/AMPS gels.

Thermogravimetric analysis (TGA) is commonly used to determine the thermal stability of materials from the initial degradation temperature (IDT; ° C.), and after degradation above 650° C. (RS; wt. %) to determine the amount of organic and polymeric materials. Thermal stability of the modified AG and MR nanogels was evaluated from their TGA thermograms as represented in FIGS. 3A and 3B, respectively. The thermal stability was estimated from initial degradation temperature (IDT; ° C.) and the remained residual contents above 750° C. (RS %; Wt.%). In this respect, the IDTs of AG, AG-NIPAm/AMPS, AG-NIPAm/4-VP-AMPS and AG-NIPAm/VIm-AMPS are 240° C., 220° C., 265° C., and 300° C., respectively. Moreover, it was found that AG, AG-NIPAm/AMPS, AG-NIPAm/4-VP-AMPS and AG-NIPAm/VIm-AMPS lose approximately 15 wt. %, 10 wt. %, 2 wt. %, and 1 wt. %, respectively from their original weights below 150° C. that referred to humidity or water contents. These data mean that the increasing degree of crosslinking decreases the hydrophilicity and water contents of the modified AG nanoparticles. It was also noticed that in contrast to the unmodified AG that showed two-stage degradation steps without RS %, the AG-NIPAm/AMPS, AG-NIPAm/4-VP-AMPS and AG-NIPAm/VIm-AMPS nanogels exhibited multistep degradation steps with a RS % of 15 wt. %, 20 wt. %, and 28 wt. %, respectively (FIG. 3A). Therefore, it may be concluded that the AG nanogels thermal stability increased in the order AG-NIPAm/VIm-AMPS>AG-NIPAm/4-VP-AMPS>AG-NIPAm/AMPS due to lowering of basicity with the formation of organic salts.

Referring to FIG. 3B, the MR nanogel thermograms show that the modification of MR with nanogels increases its hydrophilicity due to increasing the Wt. % lose below 150° C. in this case MR-NIPAm/AMPS>MR-NIPAm/4-VP-AMPS>MR-NIPAm/AMPS. These data also confirm the lower crosslinking densities of MR nanogels more than GA nanogels. Moreover, it is also concluded that the isopropyl groups of NIPAm were oriented to the outer surfaces of AG more than MR to decrease the hydrophobicity of GA nanogels. The RS % of the MR-NIPAm/AMPS, MR-NIPAm/4-VP-AMPS and MR-NIPAm/VIm-AMPS nanogels are 25 wt. %, 30 wt. %, and 35 wt. %, respectively. These data confirm that the grafting of MR with nanogels was more than what occurred with GA.

Figure 5A:
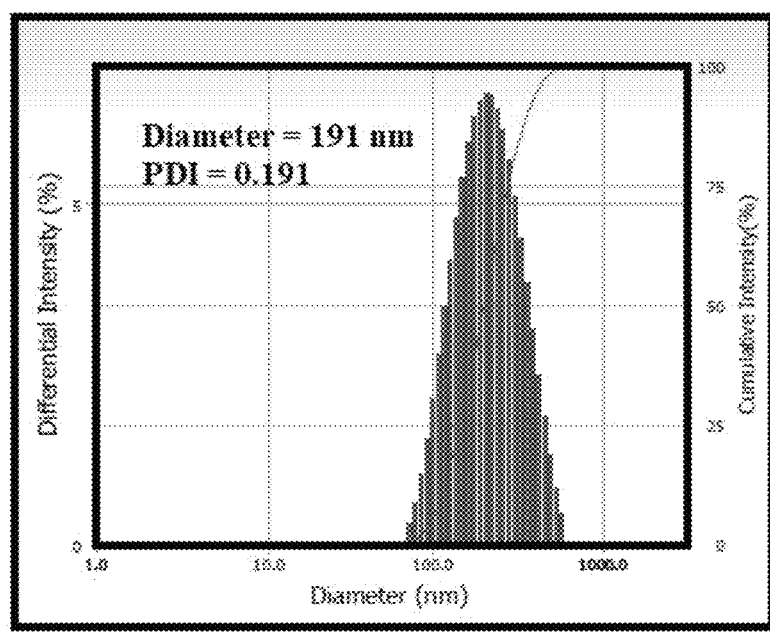
FIG. 5A is a DLS graph showing particle size of GA-NIPAm/VIm-AMPS gels.
Figure 5B:
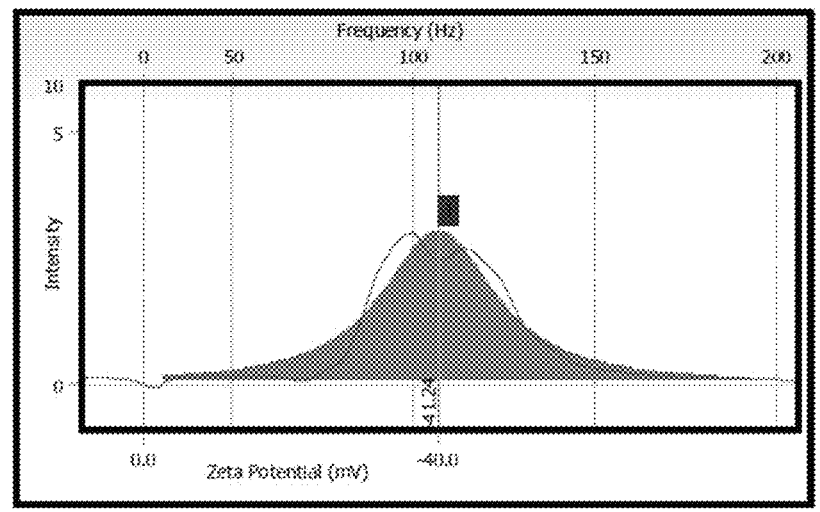
FIG. 5B is a DLS graph showing zeta potential of GA-NIPAm/VIm-AMPS gels.
Figure 6A:
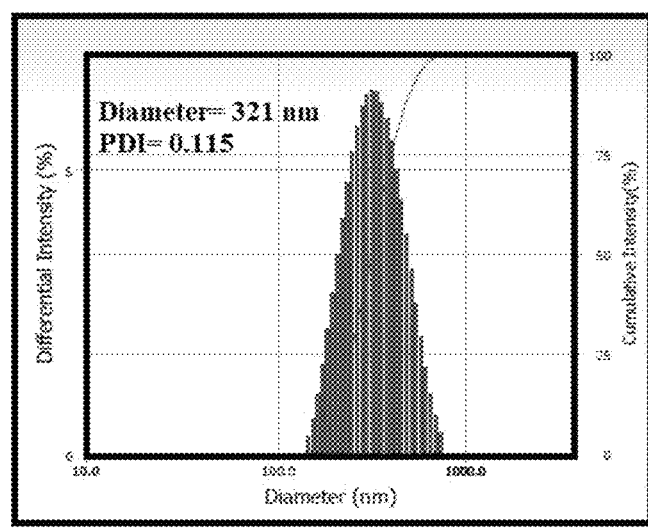
FIG. 6A is a DLS graph showing particle size of GA-NIPAm/4-VP-AMPS gels.
Figure 6B:
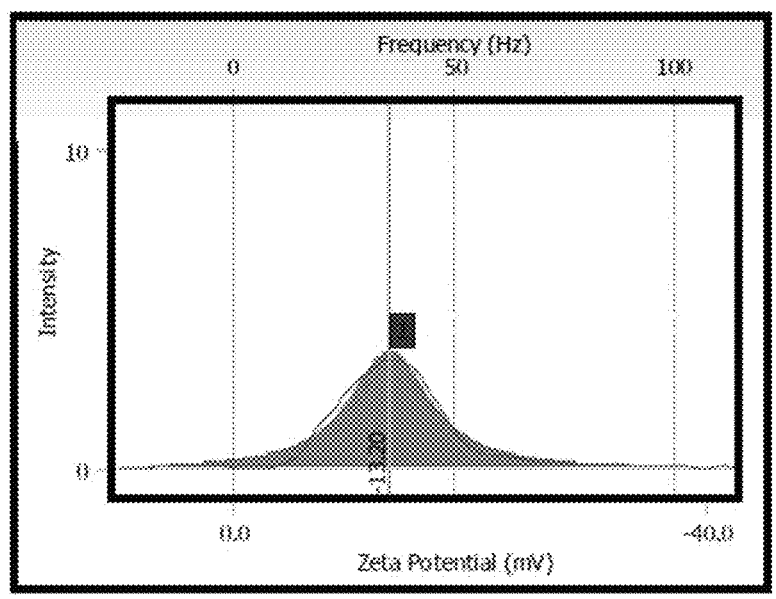
FIG. 6B is a DLS graph showing zeta potential of GA-NIPAm/4-VP-AMPS gels.
Figure 7A:
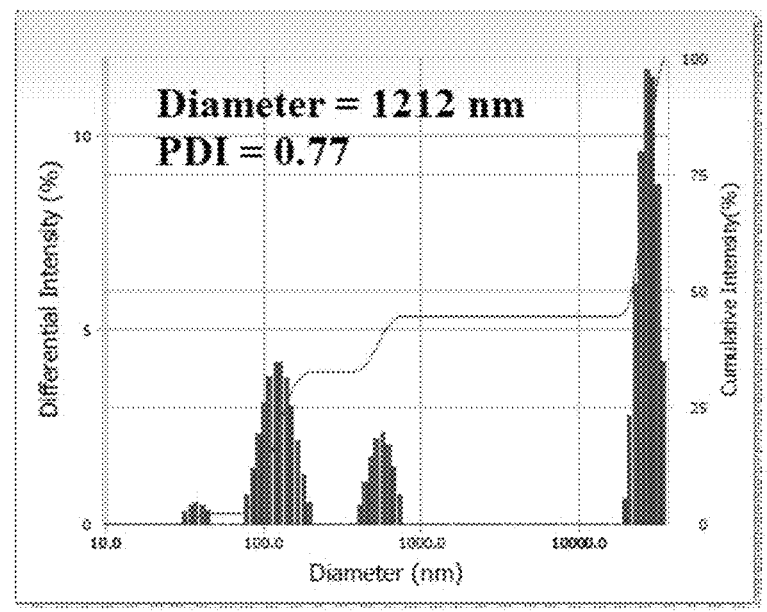
FIG. 7A is a DLS graph showing particle size of MR-NIPAm/AMPS gels.
Figure 7B:
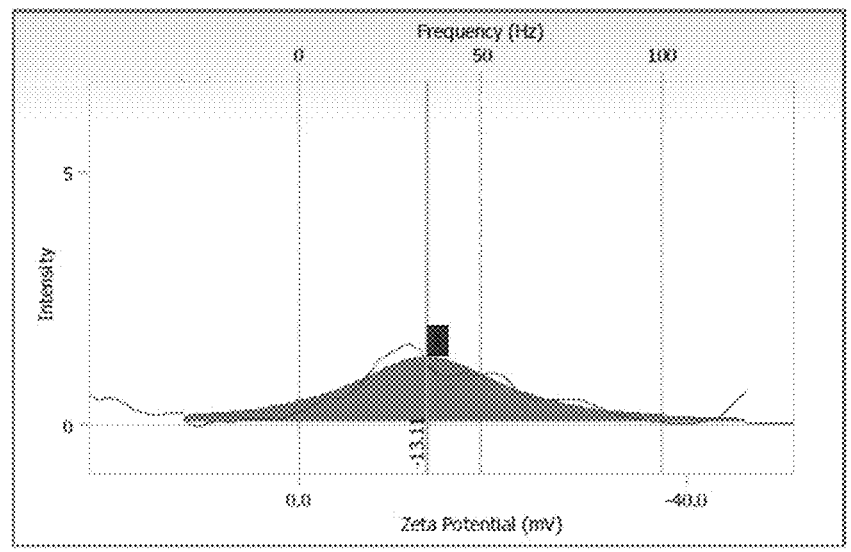
FIG. 7B is a DLS graph showing zeta potential of MR-NIPAm/AMPS gels.

The particle sizes, diameters, and polydispersity index (PDI) as well as surfaces charges (zeta potentials; mV) of GA or MR gels were measured from their DLS and represented in FIGS. 4A-4B, 5A-5B, and 6A-6B, respectively. The particle sizes and PDI of GA-NIPAm/AMPS, GA-NIPAm/VIm-AMPS and GA-NIPAm/4-VP-AMPS (listed in FIGS. 4A-4B and 5A-5B) show that their diameters were decreased due to contribution of P-IL. Moreover, their negative surface charges became more negative in case of GA-NIPAm/VIm-AMPS (-41 mV; FIG. 5B). It is well established that the suspensions or dispersions having zeta potential>25 mV and <-25 mV are stable in their aqueous solutions. Hence it can be concluded that the GA-NIPAm/VIm-AMPS nanogel suspension is stable at particle volume concentration of 0.1% due to its smaller particle volume fraction, and more negative zeta potential. It can be stated that GA-NIPAm/VIm-AMPS forms monodisperse nanogels; hence the interaction of the particle to agglomerate is smaller. The GA-NIPAm/AMPS (FIG. 4A) having higher particle size diameters and PDI confirm that it can be swelled in water and forms agglomerates due to the hydrogen bonding of AMPS or NIPAm sulfonic and amide groups with water. While the formation of organic salt in case of GA-NIPAm/4-VP-AMPS (FIG. 6A) forms monodisperse microgels but the higher electrostatic attraction forces due to their lower zeta potentials is responsible on its lower stability in the aqueous solutions. In contrast to the GA nanogels, it is noticed that MR extract form polydisperse gels having higher particle size diameters and lower zeta potential, as represented in case of MR-NIPAm/AMPS (FIG. 7A-7B). This can be explained on the basis that the lower crosslinking densities on the MR surfaces cannot hinder the interaction between the particles in the suspension and leads to agglomeration.

Figure 8A:
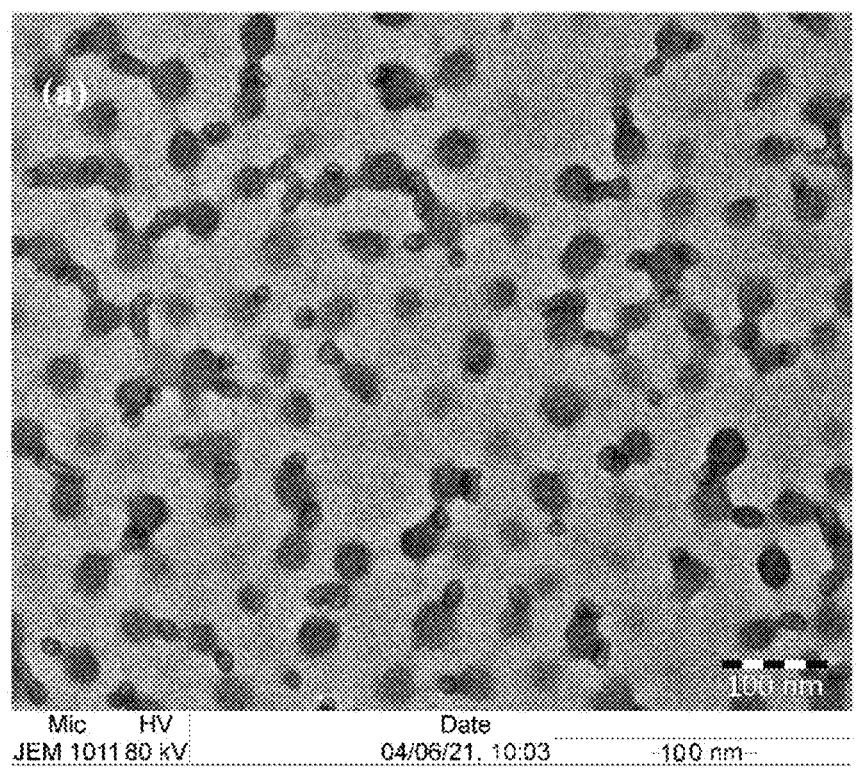
FIGS. 8A-8D are transmission electron microscopy (TEM) micrographs of A) GA-NIPAm/AMPS (90/10), B) GA-NIPAm/VIm-AMPS (80/10-10), C) GA-NIPAm/VIm-AMPS (90/5-5), and D) GA-NIPAm/4-VP-AMPS (90/5-5).
Figure 8B:
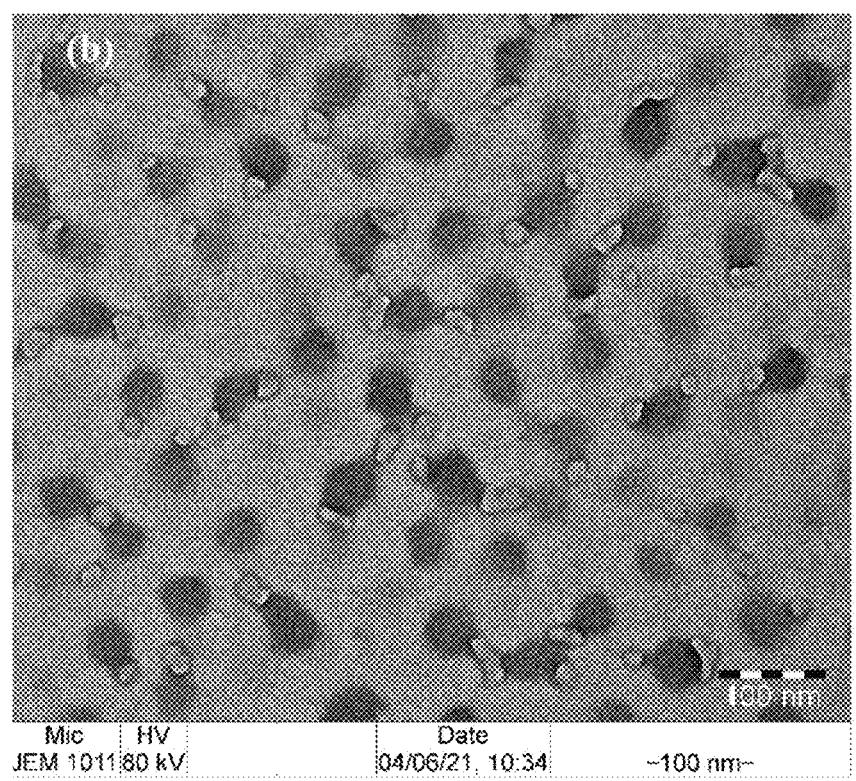
Figure 8C:
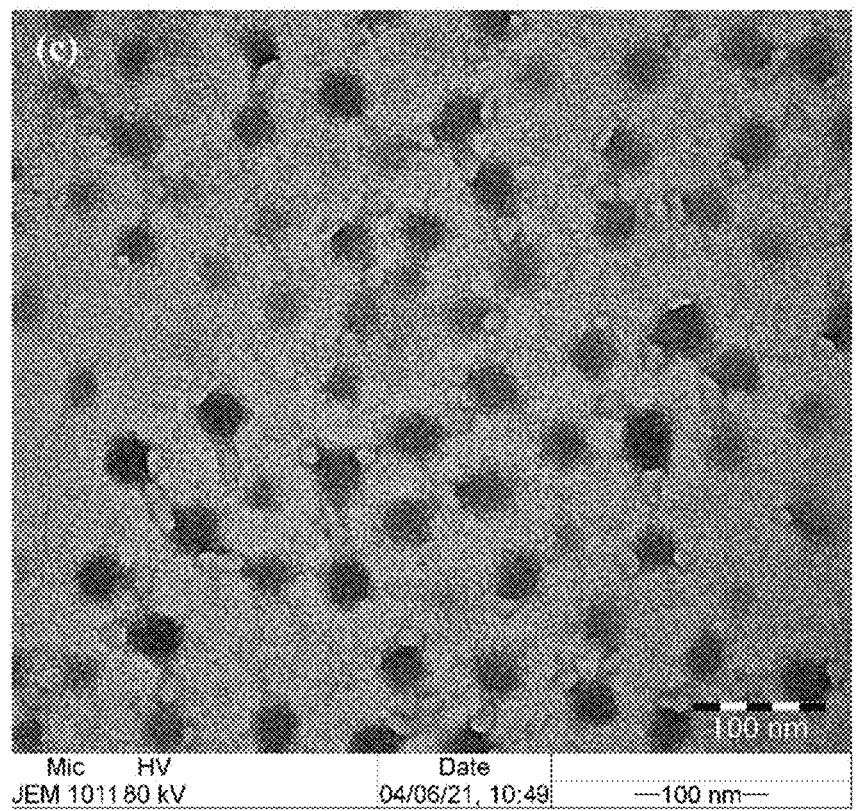
Figure 8D:
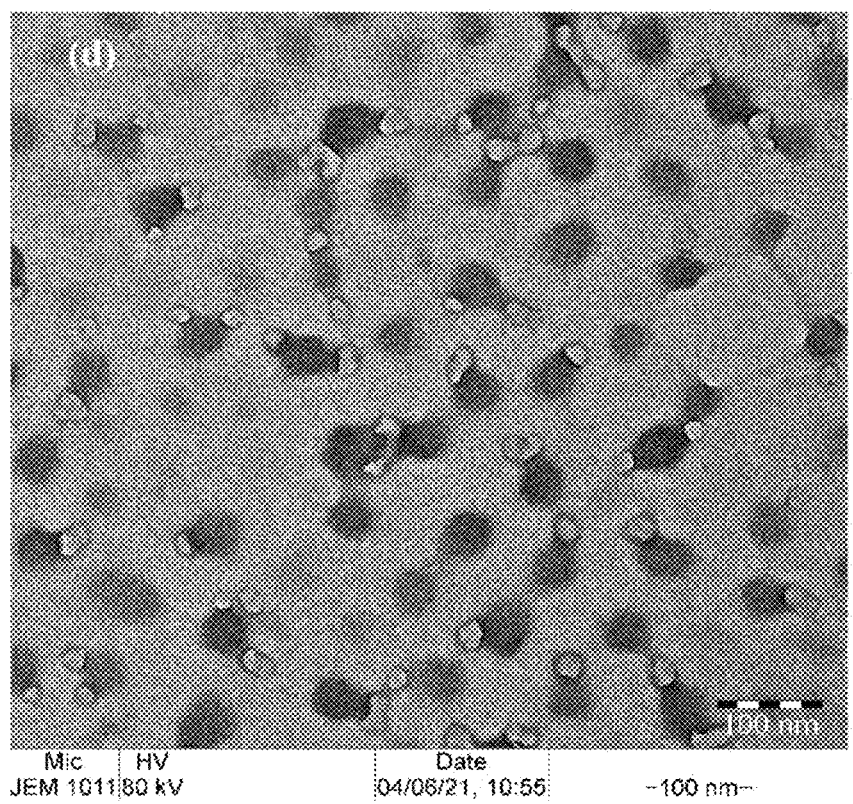
Figure 9A:
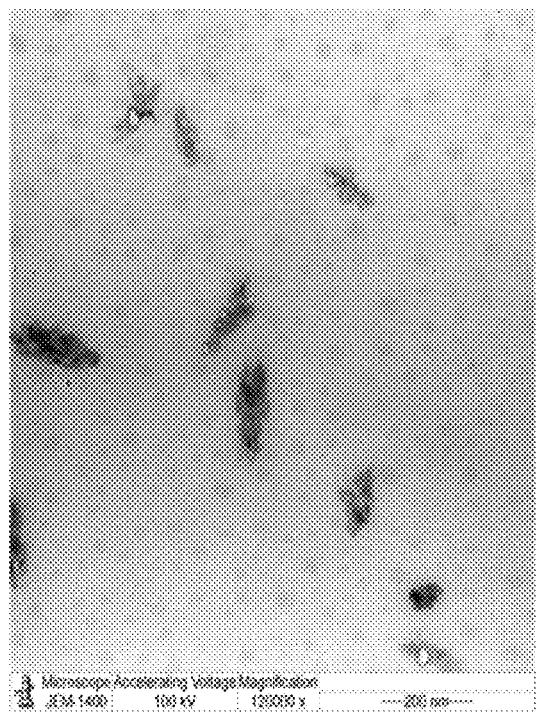
FIGS. 9A-9D are TEM micrographs of A) MR-NIPAm/AMPS (90/10), B) MR-NIPAm/VIm-AMPS (80/10-10), C) MR-NIPAm/VIm-AMPS (90/5-5), and D) MR-NIPAm/4-VP-AMPS (90/5-5).
Figure 9B:
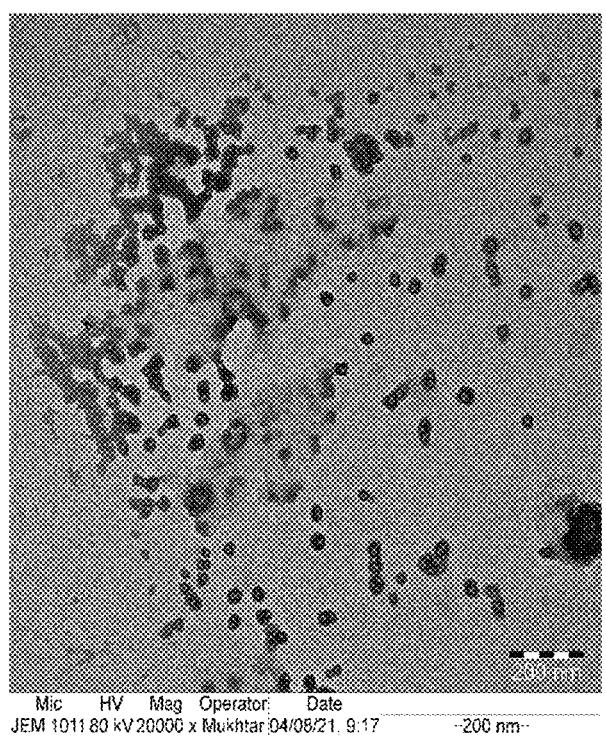
Figure 9C:
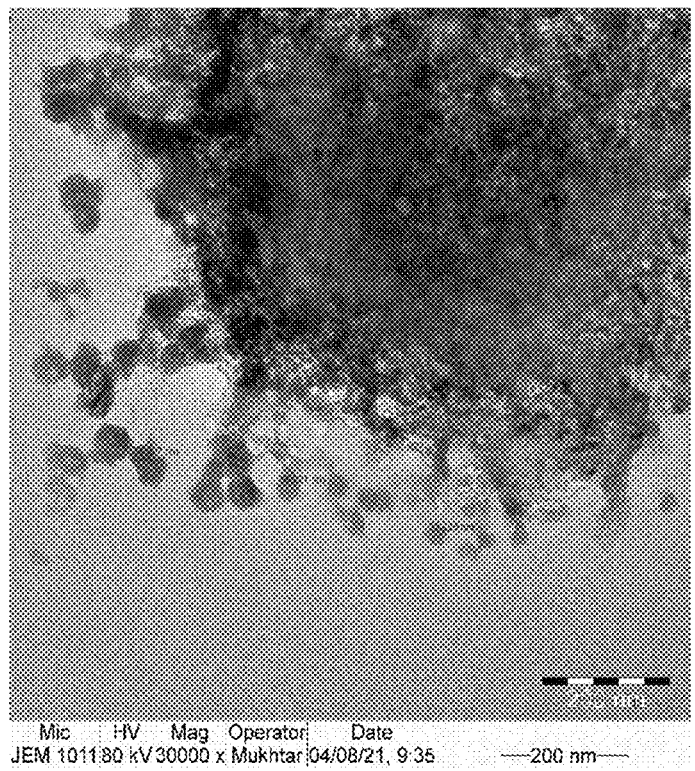
Figure 9D:
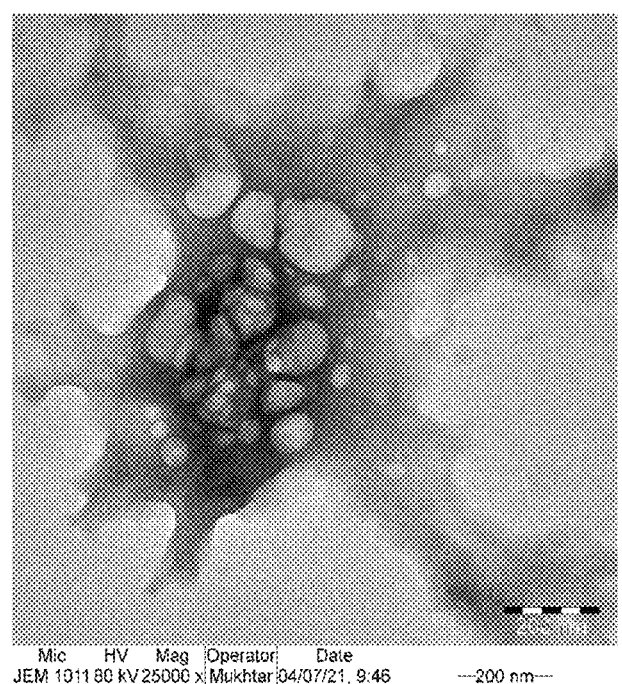
Figure 10A:
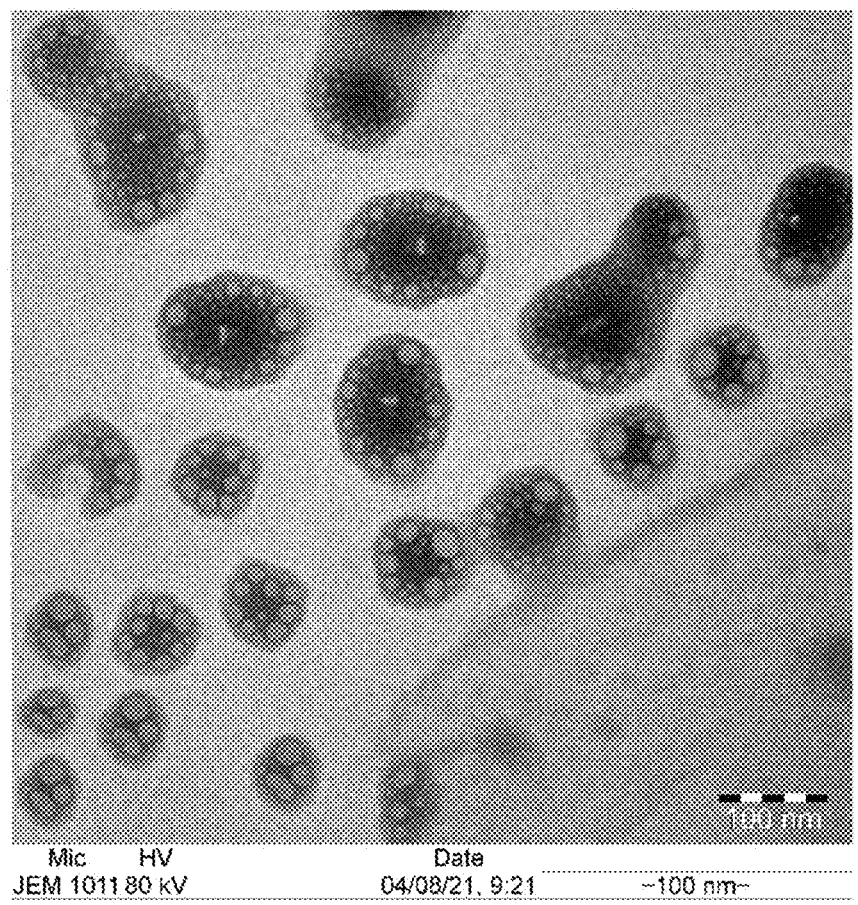
FIG. 10A-10D are TEM micrographs of insulin loaded A) AG-NIPAm/AMPS (90/10), B) MR-NIPAm/AMPS, C) GA-NIPAm/4-VP-AMPS (90/5-5) and D) GA-NIPAm/VIm-AMPS (90/5-5).
Figure 10B:
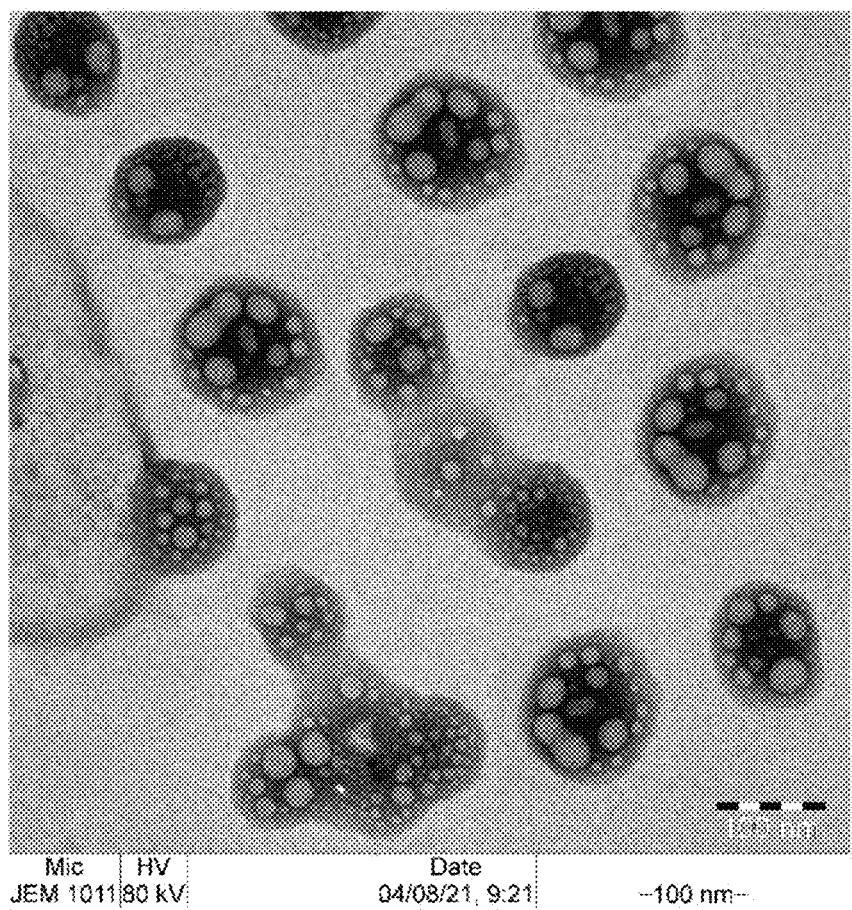
Figure 10C:
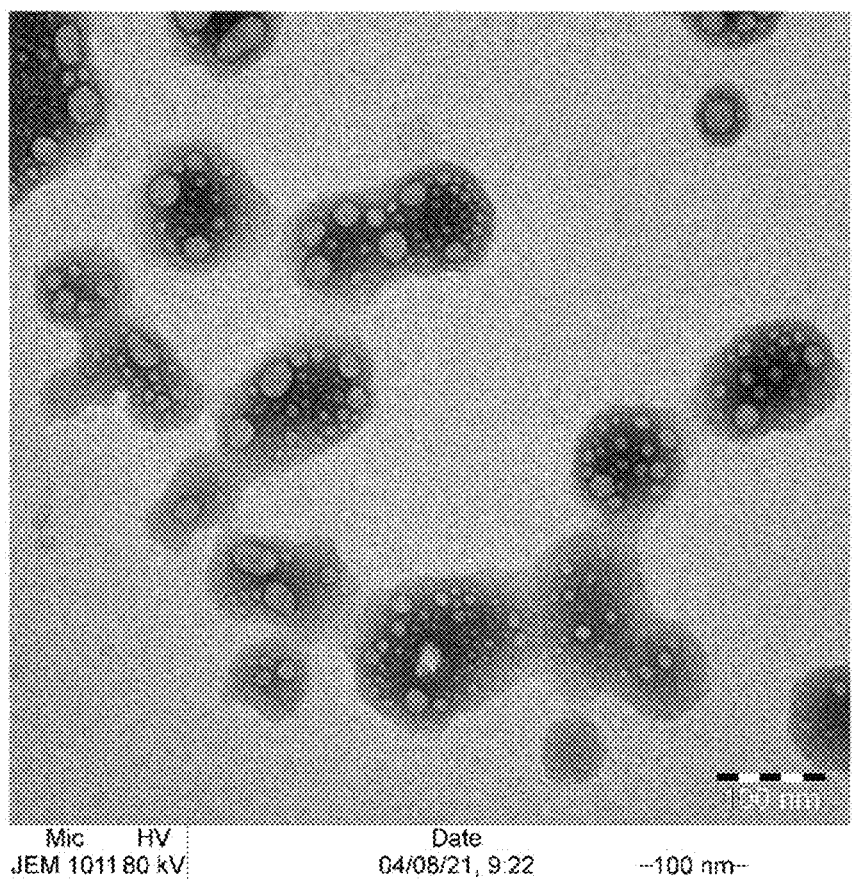
Figure 10D:
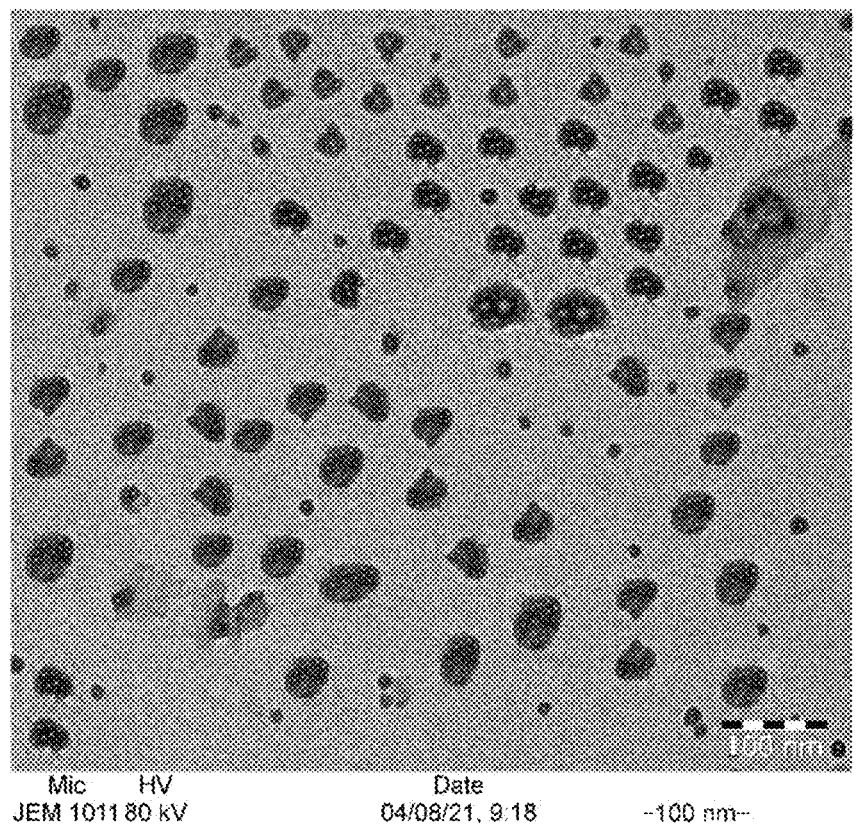

The crosslinking of NIPAm and AMPS with MBA or P-ILs to form gels or their chemical linking with AG or MR, as illustrated in schemes 1 and 2, can be elucidated from their morphologies as summarized from their TEM micrographs (FIGS. 8A-8D and 9A-9D). In this respect, the morphologies of the modified AG-NIPAm/AMPS (90/10), AG-NIPAm/VIm-AMPS (80/10-10), AG-NIPAm/VIm-AMPS (90/5-5), and AG-NIPAm/4-VP-AMPS (90/5-5) (FIGS. 8A-8D) show formation of the spherical morphologies. It was also noticed the NIPAm/AMPS, NIPAm/VIm-AMPS or NIPAm/4-VP-AMPS were linked on the periphery of the spherical particles as white eclipsed spherical particles. It was also noticed that AG-NIPAm/VIm-AMPS (90/5-5) (FIG. 8C) form monodisperse AG nanogels without formation of separate particles of NIPAm/VIm-AMPS (90/5-5) gel. The NIPAm/4-VP-AMPS (90/5-5) produced agglomerates when linked with AG (FIG. 8D). The modified MR gels with the NIPAm/AMPS, NIPAm/VIm-AMPS or NIPAm/4-VP-AMPS (FIGS. 9A-9D) show different morphologies than AG to confirm their DLS data (FIG. 7A-7B). It was noticed the MR gels forms both polymer gels and modified MR gels that are responsible for agglomeration in the aqueous solutions.

Example 5

Loading Insulin

Insulin loading was accomplished by immersing the synthesized modified gels (prepared by the methods described above) (0.5 g) in 1 mL (100 International Unit; IU) insulin solution under stirring for 24 hours at room temperature. The gel suspension was filtered and washed with deionized water. Free insulin was measured in the supernatant by using UV spectrophotometer at 284 nm. The insulin encapsulation efficiency (IE %) was calculated by the following equation:

$$IE\ (\%) = [(\text{Total amount of insulin}) - (\text{free insulin in the supernatant})] / [(\text{Total amount of insulin})] \times 100$$

Example 6

Insulin Release

To determine the amount of insulin released (IR %) from the modified gels prepared as described above, a dialysis membrane was used. In this respect, the insulin-loaded gels (0.5 g) were placed in the dialysis bag (length 12 cm, MWCO 14000) containing 2 mL of buffer solution pH 7.4. The dialysis bag was filled with the insulin loaded gel and immersed in either synthetic stomach fluid (SSF) or simulated intestinal fluid (SIF) solution (13 mL). The solutions were incubated in a water-bath at 37° C. under stirring. The insulin release was determined at different interval times ranging from 1 to 24 hours. An aliquot (250 µL) of the SSF or SIF solution was removed and replaced with fresh medium. The insulin concentrations of the aliquots were determined using UV, and the cumulative amount of insulin released from the nanoparticles was also calculated by UV as represented in equation 2:

$$IR\ (\%) = [(\text{Total amount of loaded insulin}) - (\text{free insulin in the aliquot})] / [(\text{Total amount of loaded insulin})] \times 100$$

The insulin release of the loaded gels at pH 1.2 was determined as well as described at pH 7.4. The insulin was loaded as a blank sample without gels into a dialysis membrane at pH levels of pH 1.2 and 7.4.

The present characterization data show that either modified AG or MR gels that do not contain monomers will be biocompatible. Moreover, the presence of negative charges on their surfaces as determined from their zeta potentials data (FIGS. 4-7) facilitate their higher muco-adhesion in the small intestine and also exhibited better intestinal permeability as well as greater performance than positively charged chitosan nanogels. Moreover, it has also been reported that negative surface charges of nanoparticles are more effective on blood glucose level administration than those that possess positive charges. Incorporation of hydrophobic polymers based on VIm, 4-VP, and NIPAm as well as ionic monomers such as AMPS, AA or MAA produce pH and temperature sensitive nanogels that can protect the loaded insulin from SSF. The morphologies of the modified AG and MR (FIGS. 8 and 9) show the core-shell structure having a different degree of cross-linking that will alter the loading and release of insulin as mentioned in the experimental section. In this respect, the insulin encapsulation efficiency (IE %) at equilibrium time (ET; h) for the modified AG and MR were determined and are summarized in Table 1.

TABLE 1

The insulin encapsulation efficiency (IE %) at equilibrium time (ET; h) of modified AG and MR at 20° C.

| Naonogels | IE (%) | ET (h) |
|---|---|---|
| AG-NIPAm/AMPS (90/10) | 100 | 24 |
| AG-NIPAm/VIm-AMPS (90/5-5) | 75 | 5 |
| AG-NIPAm/4-VP-AMPS (90/5-5) | 70 | 10 |
| MR-NIPAm/AMPS (90/10) | 52 | 24 |

The data summarized in Table 1 elucidate that the IE (%) were higher in the order AG-NIPAm/AMPS (90/10)>AG-NIPAm/VIm-AMPS (90/5-5)>AG-NIPAm/4-VP-AMPS (90/5-5)>MR-NIPAm/AMPS (90/10). It is well known that insulin has dimer chain two peptide chains linked with two di-sulfide bonds. One of the chains is composed of 21 amino acids and the other contains 30 amino acids. The loading of negatively charged insulin into electrolyte AG or MR will be affected by electrostatic interactions and formation of complexes as well as crosslinking densities of gels. The driving force for complexation of insulin with polyelectrolyte nanogels was attributed to the hydrophobic nature of nanogels. Accordingly, the higher loading of insulin with AG-NIPAm/AMPS (90/10) than MR-NIPAm/AMPS (90/10), Table 1, can be referred to the hydrophobic nature of AG more than MR gels. It was also noticed that the diffusion of insulin into AG-NIPAm/VIm-AMPS (90/5-5) was much faster (lower ET; Table 1) and this can be attributed to the presence of zwitter ionic characters, beside their lower particle sizes as well as higher surfaces charges. These data were elucidated from TEM data of insulin loaded AG and MR gels represented in FIGS. 10A-10D.

Figure 11A:
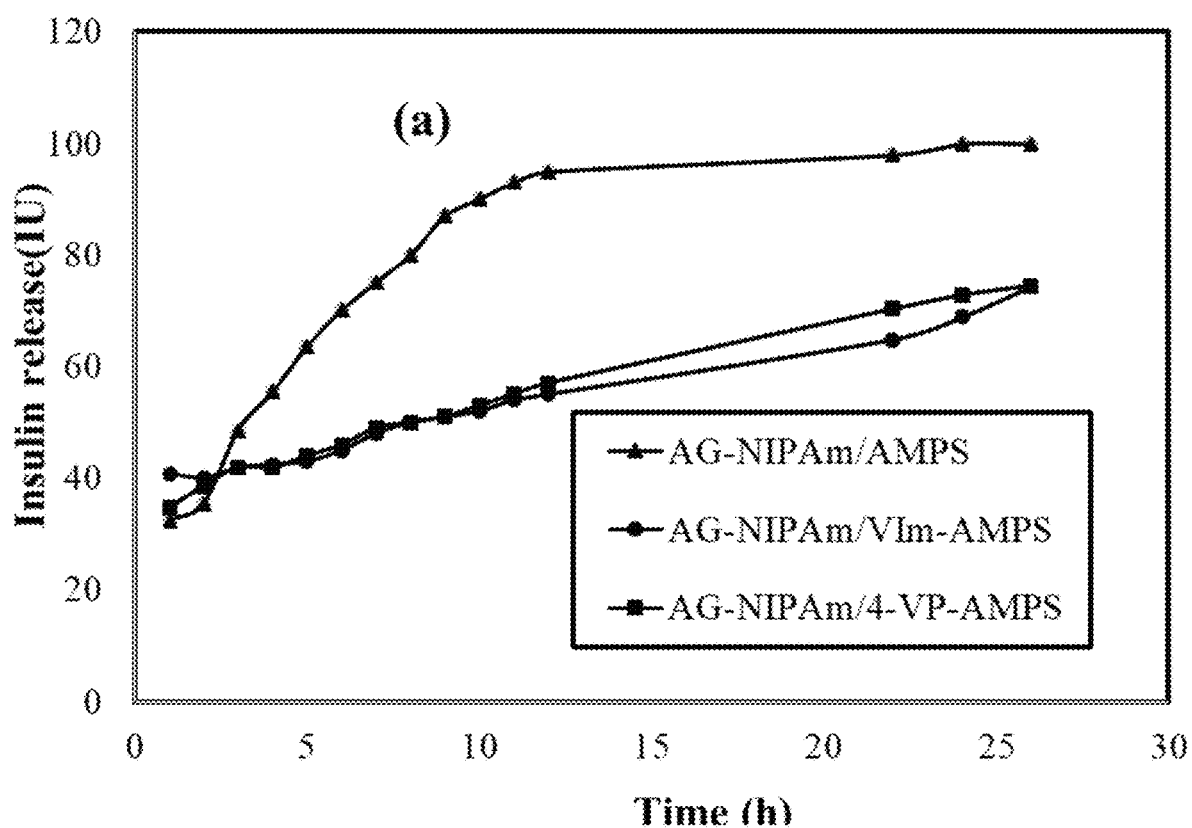
FIG. 11A is a graph of insulin release of GA nanogels in simulated intestinal fluid (SIF) at 37° C.
Figure 11B:
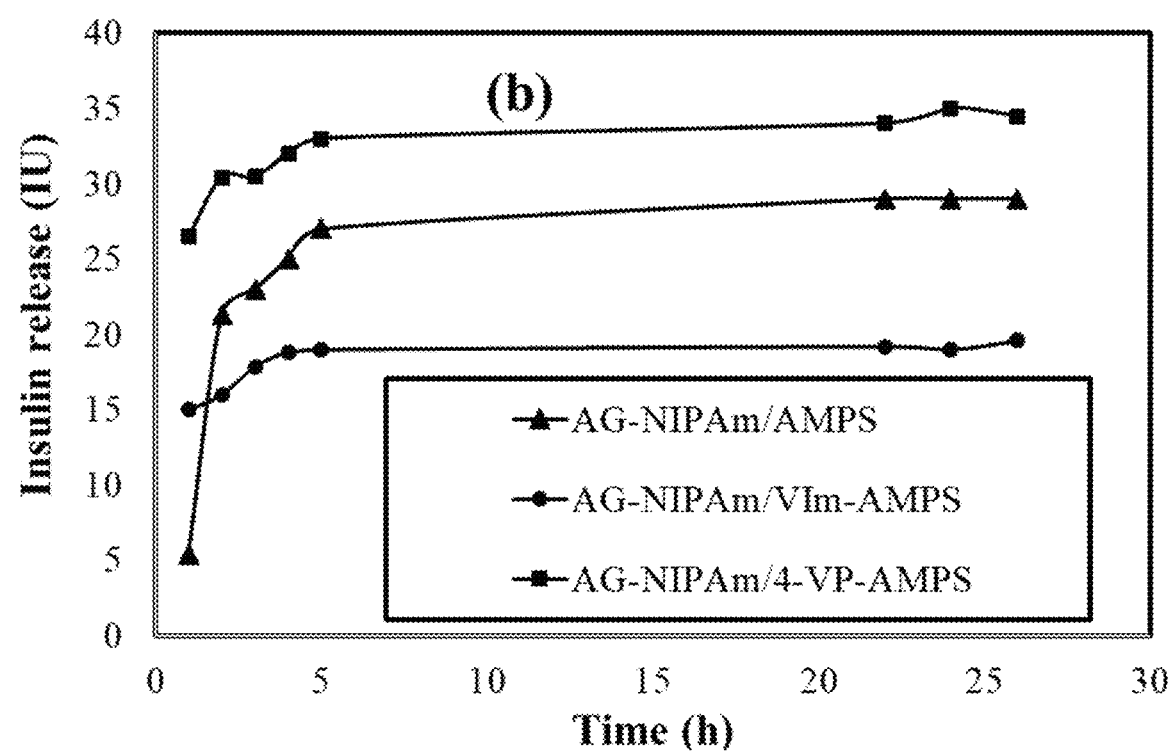
FIG. 11B is a graph of insulin release of GA nanogels in synthetic stomach fluid (SSF) at 37° C.

Finally, it was observed from FIG. 11A that immediate release of insulin from the GA nanogels at pH 1.2 was retarded in case of MR-NIPAm/VIm-AMPS (FIG. 7B) releasing only 15% of encapsulated insulin during 24 hours. This may be due to the strong complexation of hydrophobic AG surfaces and ionic interactions between insulin and charges of AG-NIPAm/VIm-AMPS. This hydrophobic surface will protect the entrapped insulin from the proteolytic enzymatic degradation in the stomach. Further, the insulin loaded AG nanogels release studies at pH 6.8 and 7.4 demonstrated significant insulin release from the nanogels (FIG. 11A). The insulin release of NIPAm/VIm-AMPS was also in a sustained manner. For an initial 1 hour, 40 IU of insulin release was observed, but over 24 hours it was about 70% of the encapsulated amount. The prolonged release profile may help to produce desired effects within an in-vivo system. The pH responsive release pattern may facilitate oral administration of insulin in the in vivo model.

It is to be understood that the gum arabic and myrrh nanogels for oral delivery of insulin are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A synthesized gel, loaded with insulin, the gel comprising:
   an extract selected from the group consisting of Gum Arabic (GA) extract and myrhh (MR) extract;
   a monomer selected from the group consisting of N-Isopropylacrylamide (NIPAm) and acidic monomers;
   Ammonium persulfate (APS) initiator;
   N,N'-methylenebisacrylamide (MBA);
   a polyvinyl selected from the group consisting of quaternized N-vinyl imidazole (VIm) and 4-vinyl pyridine (4-VP) organic salt; and
   insulin.

2. The gel of claim 1, wherein the acidic monomers are selected from a group consisting of 2-acrylamido-2-methyl-1-propanesulfonicacid (AMPS), acrylic acid (AA), and methacrylic acid (MAA).

3. The gel of claim 1, wherein the gel is a microgel.

4. The gel of claim 1, wherein the gel is a nanogel.

5. The gel of claim 1, wherein the gel comprises Gum Arabic (GA) extract, N-Isopropylacrylamide (NIPAm), 2-acrylamido-2-methyl-1-propanesulfonicacid (AMPS), and a gel particle diameter is about 1950 nm.

6. The gel of claim 5, wherein an insulin encapsulation efficiency is 100% at 24 hours.

7. The gel of claim 1, wherein the gel comprises Gum Arabic (GA) extract, N-Isopropylacrylamide (NIPAm), quaternized N-vinyl imidazole (VIm), 2-acrylamido-2-methyl-1-propanesulfonicacid (AMPS), and a gel particle diameter is about 191 nm.

8. The gel of claim 7, wherein an insulin encapsulation efficiency is 75% at 5 hours.

9. The gel of claim 1, wherein the gel comprises Gum Arabic (GA) extract, N-Isopropylacrylamide (NIPAm), 4-vinyl pyridine (4-VP), 2-acrylamido-2-methyl-1-propanesulfonicacid (AMPS), and a gel particle diameter is about 321 nm.

10. The gel of claim 9, wherein an insulin encapsulation efficiency is 70% at 10 hours.

11. The gel of claim 1, wherein the gel comprises myrhh (MR), N-Isopropylacrylamide (NIPAm), 2-acrylamido-2-methyl-1-propanesulfonicacid (AMPS), and a gel particle diameter is about 1212 nm.

12. The gel of claim 11, wherein an insulin encapsulation efficiency is 52% at 24 hours.

13. A method of treating insulin dependent diabetes, comprising administering to a patient in need thereof a therapeutically effective amount of insulin loaded in the gel of claim 1.

14. The method of claim 13, wherein the gel is administered orally.

* * * * *